United States Patent [19]

Carpenter

[11] Patent Number: 5,047,592
[45] Date of Patent: Sep. 10, 1991

[54] SELECTIVE HYDROGENOLYSIS PROCESS
[75] Inventor: Joel F. Carpenter, Baton Rouge, La.
[73] Assignee: Ethyl Corporation, Richmond, Va.
[21] Appl. No.: 396,346
[22] Filed: Aug. 21, 1989
[51] Int. Cl.⁵ .................. C07C 209/68; C07C 209/78
[52] U.S. Cl. .................................................... 564/374
[58] Field of Search ........................................ 564/374

[56] References Cited

U.S. PATENT DOCUMENTS

| | | | |
|---|---|---|---|
| 1,913,520 | 7/1930 | Stolz et al. | 564/343 X |
| 2,151,459 | 3/1939 | Bockmuhl et al. | 564/35 X |
| 2,308,232 | 1/1940 | Schening et al. | 564/358 X |
| 3,809,714 | 5/1974 | Hussain et al. | 564/343 X |
| 4,374,149 | 2/1983 | Phillion | 564/374 X |

OTHER PUBLICATIONS

Wayner et al., "Synthetic Organic Chemistry", p. 6, (1963).
Rao et al., Tetrahedron, vol. 38, No. 24, (1982), pp. 3555-3561.
Horning et al., JACS, vol. 71, (1949), pp. 1036-1037.
Norlander et al., J. Org. Chem., vol. 49, No. 22, (1984), pp. 4107-4111.
Rosenmund et al., Chem. Ber., vol. 75, (1942), pp. 1850-1859.
Burdeska, Synthesis, (1982), pp. 940-942.
Wong et al., Canadian Journal of Chemistry, vol. 49, (1971), pp. 2712-7218.

*Primary Examiner*—Richard L. Raymond
*Attorney, Agent, or Firm*—Richard J. Hammond; John F. Sieberth

[57] ABSTRACT

A relatively simple, economical process for the synthesis of epinine and related compounds is described. The process involves subjecting adrenalone, epinephrine or their respective congeners to selective hydrogenolysis using hydrogen and a metal hydrogenolysis catalyst such as palladium, platinum, rhodium or nickel. Preferably the reaction is conducted in a non-oxidizing acidic liquid reaction medium, such as in aqueous hydrochloric acid.

14 Claims, No Drawings

SELECTIVE HYDROGENOLYSIS PROCESS

TECHNICAL FIELD

This invention relates to and provides a novel process for the production of epinine and related compounds.

BACKGROUND

Epinine and related compounds of the formula

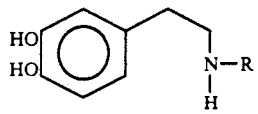
(I)

wherein R is a hydrogen atom or a hydrocarbyl group such as alkyl, aryl, cycloalkyl, aralkyl, alkenyl, cycloalkenyl, etc., can be oxidatively cyclized to bicyclic quinones, which in turn can be isomerized to the 5,6-dihydroxindoles, a group of compounds useful as dyes and/or dye intermediates, and as antioxidants and oxygen getters for organic systems. For example, epinochrome, a deep-red water-soluble compound, can be formed by the oxidative cyclization of epinine (Formula I above; R=methyl) and then isomerized to 5,6-dihydroxyindole—see Wyler et al, *Helv. Chem. Acta* 1968, 51, 1476. Improved processes for effecting the conversion of compounds of Formula I to 1H-indole-5,6-diones, 5,6-dihydroxyindoles, and 5,6-diacyloxyindoles, are described in my co-pending applications Ser. Nos. 396,345 and 396,139, filed contemporaneously herewith, both now abandoned. In addition to these utilities, compounds of Formula I have application as adrenergics, and particularly as vasoconstrictors.

Unfortunately the compounds of Formula I above are quite expensive and difficult to prepare. See the procedures described by Pyman, *J. Chem. Soc.* 1909, 95, 166; Buck, *J. Am. Chem. Soc.* 1930, 4119; and Bretschneider, *Monatsh.* 1947, 76, 335, which involve inefficient chemistry with functional group protections and deprotections.

A welcome contribution to the art would be the provision of a new and highly efficient method for the synthesis of compounds of Formula I above.

THE INVENTION

Accordingly an object of this invention is to provide a relatively simple, more economical process for the synthesis of the compounds of Formula I above, especially epinine itself.

Pursuant to this invention, compounds of Formula I above are readily produced in good yield by selective hydrogenolysis of compounds of the formula

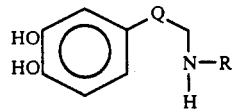
(II)

where Q is either a carbonyl group

or a hydroxymethylene group

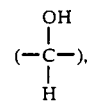

and R is as above described. This reaction is conducted using hydrogen and a metal hydrogenolysis catalyst such as palladium, platinum, rhodium, nickel, or the like. Such catalysts are preferably used in the form of supported catalysts, such as Pd on carbon, Pt on carbon, etc. While other conditions are suitable and may be used in the practice of this invention, the hydrogenolysis is best conducted in a non-oxidizing acidic liquid reaction medium, such as in aqueous hydrochloric acid, aqueous phosphoric acid, benzene sulfonic acid, toluene sulfonic acid, dilute sulfuric acid, and the like. Consequently, the products of Formula I above will often be produced in the form of their salts, such as the hydrochlorides, phosphates, etc.

It will be understood and appreciated by those skilled in the art that, if desired, the two vicinal hydroxyl groups may be substituted by protecting groups (e.g., univalent hydrocarbyl groups, acyl groups, silyl groups, etc. or they may be bridged by a methylene or other suitable divalent hydrocarbyl group). However, a feature of this invention is that use of such protecting groups is not required—when conducted under the proper conditions, the reaction produces the desired product in high yield and with good selectivity. It will also be understood and appreciated by those skilled in the art that, if desired, the aromatic ring in Formula II above may be substituted by innocuous groups—that is, groups such as alkyl, aryl, cycloalkyl, fluoro, chloro, amino, alkylamino, dialkylamino, arylamino, etc., which do not interfere with or prevent the desired hydrogenolysis reaction.

The reaction is usually conducted at a temperature in the range of about 20° to about 100° C. (preferably in the range of about 60° to about 80° C.) and at a pressure of up to about 100 psi (preferably in the range of about 40 to about 60 psi). Departures may be made from such temperature and/or pressure conditions whenever such departures are deemed justifiable or expedient under the particular circumstances involved. Thus this invention is not to be limited to any given specific set of reaction conditions. Any set of hydrogenolysis conditions that give the desired results may be used. The process may be conducted on a batch, semi-continuous, or continuous basis. Ordinarily it will be conducted at a suitable temperature in a closed system under autogenous pressure.

Compounds of Formula II which may be utilized in the above hydrogenolysis process include:
3,4-dihydroxy-alpha-methylaminoacetophenone (adrenalone)
3,4-dihydroxy-alpha-aminoacetophenone
3,4-dihydroxy-alpha-ethylaminoacetophenone
3,4-dihydroxy-alpha-propylaminoacetophenone
3,4-dihydroxy-alpha-isopropylaminoacetophenone
3,4-dihydroxy-alpha-butylaminoacetophenone
3,4-dihydroxy-alpha-isobutylaminoacetophenone
3,4-dihydroxy-alpha-sec-butylaminoacetophenone
3,4-dihydroxy-alpha-tert-butylaminoacetophenone
3,4-dihydroxy-alpha-pentylaminoacetophenone
3,4-dihydroxy-alpha-hexylaminoacetophenone
3,4-dihydroxy-alpha-heptylaminoacetophenone 3,4-dihydroxy-alpha-octylaminoacetophenone
3,4-dihydroxy-alpha-decylaminoacetophenone
3,4-dihydroxy-alpha-dodecylaminoacetophenone
3,4-dihydroxy-alpha-tetradecylaminoacetophenone
3,4-dihydroxy-alpha-hexadecylaminoacetophenone
3,4-dihydroxy-alpha-octadecylaminoacetophenone
3,4-dihydroxy-alpha-allylaminoacetophenone
3,4-dihydroxy-alpha-butenylaminoacetophenone
3,4-dihydroxy-alpha-octenylaminoacetophenone
3,4-dihydroxy-alpha-phenylaminoacetophenone
3,4-dihydroxy-alpha-(o-tolylamino)acetophenone
3,4-dihydroxy-alpha-(m-tolylamino)acetophenone
3,4-dihydroxy-alpha-(p-tolylamino)acetophenone
3,4-dihydroxy-alpha-(2',3'-xylylamino)acetophenone
3,4-dihydroxy-alpha-(2',4'-xylylamino)acetophenone
3,4-dihydroxy-alpha-(2',5'-xylylamino)acetophenone
3,4-dihydroxy-alpha-(2',6'-xylylamino)acetophenone
3,4-dihydroxy-alpha-(3',4'-xylylamino)acetophenone
3,4-dihydroxy-alpha-(3',5'-xylylamino)acetophenone
3,4-dihydroxy-alpha-(o-fluorophenylamino)acetophenone
3,4-dihydroxy-alpha-(m-fluorophenylamino)acetophenone
3,4-dihydroxy-alpha-(p-fluorophenylamino)acetophenone
3,4-dihydroxy-alpha-(o-chlorophenylamino)acetophenone
3,4-dihydroxy-alpha-(m-chlorophenylamino)acetophenone
3,4-dihydroxy-alpha-(p-chlorophenylamino)acetophenone
3,4-dihydroxy-alpha-(o-bromophenylamino)acetophenone
3,4-dihydroxy-alpha-(m-bromophenylamino)acetophenone
3,4-dihydroxy-alpha-(p-bromophenylamino)acetophenone
3,4-dihydroxy-alpha-(2'-chloro-4'-methylamino)acetophenone
3,4-dihydroxy-alpha-(p-trifluoromethylphenylamino)acetophenone
3,4-dihydroxy-alpha-(2',6'-dichlorophenylamino)acetophenone
3,4-dihydroxy-alpha-(2',4',5'-trichlorophenylamino)acetophenone
3,4-dihydroxy-alpha-(2',4',6'-trichlorophenylamino)acetophenone
3,4-dihydroxy-alpha-(pentachlorophenylamino)acetophenone
3,4-dihydroxy-alpha-(o-methoxyphenylamino)acetophenone
3,4-dihydroxy-alpha-(p-methoxyphenylamino)acetophenone
3,4-dihydroxy-alpha-(o-phenoxyphenylamino)acetophenone
3,4-dihydroxy-alpha-(p-phenoxyphenylamino)acetophenone
3,4-dihydroxy-alpha-(cyclopentylamino)acetophenone
3,4-dihydroxy-alpha-(cyclohexenylamino)acetophenone
3,4-dihydroxy-alpha-(phenethylamino)acetophenone
3,4-dihydroxy-alpha-(cyclopropylcarbinylamino)acetophenone
3,4-dihydroxy-alpha-(1-naphthylamino)acetophenone
3,4-dihydroxy-alpha-(2-naphthylamino)acetophenone
3,4-dihydroxy-alpha-(biphenylylamino)acetophenone
3,4-dihydroxy-2-methyl-alpha-ethylaminoacetophenone
3,4-dihydroxy-2,5-dimethyl-alpha-propylaminoacetophenone
3,4-dihydroxy-2-phenyl-alpha-isopropylaminoacetophenone
3,4-dihydroxy-2-phenoxy-alpha-butylaminoacetophenone
3,4-dihydroxy-5-methyl-alpha-ethylaminoacetophenone
3,4-dihydroxy-5-phenyl-alpha-methylaminoacetophenone
3,4-dihydroxy-2-methoxy-alpha-methylaminoacetophenone
3,4-dihydroxy-2-chloro-5-ethyl-alpha-methylaminoacetophenone
3,4-dihydroxy-2-trifluoromethyl-alpha-methylaminoacetophenone
3,4-dihydroxy-2,5-difluoro-alpha-tert-butylaminoacetophenone
3,4-dihydroxy-alpha-[(methylamino)methyl]-benzyl alcohol (epinephrine)
3,4-dihydroxy-alpha-(aminomethyl)-benzyl alcohol
3,4-dihydroxy-alpha-[(ethylamino)methyl]-benzyl alcohol
3,4-dihydroxy-alpha-[(propylamino)methyl]-benzyl alcohol
3,4-dihydroxy-alpha-[(isopropylamino)methyl]-benzyl alcohol
3,4-dihydroxy-alpha-[(butylamino)methyl]-benzyl alcohol
3,4-dihydroxy-alpha-[(octylamino)methyl]-benzyl alcohol
3,4-dihydroxy-alpha-[(eicosylamino)methyl]-benzyl alcohol
3,4-dihydroxy-alpha-[(allylamino)methyl]-benzyl alcohol
3,4-dihydroxy-alpha-[(dodecenylamino)methyl]-benzyl alcohol
3,4-dihydroxy-alpha-[(phenylamino)methyl]-benzyl alcohol
3,4-dihydroxy-alpha-[(o-tolylamino)methyl]-benzyl alcohol
3,4-dihydroxy-alpha-[(m-tolylamino)methyl]-benzyl alcohol
3,4-dihydroxy-alpha-[(p-tolylamino)methyl]-benzyl alcohol
3,4-dihydroxy-alpha-[(2',3'-xylylamino)methyl]-benzyl alcohol
3,4-dihydroxy-alpha-[(2',5'-xylylamino)methyl]-benzyl alcohol
3,4-dihydroxy-alpha-[(3',4'-xylylamino)methyl]-benzyl alcohol
3,4-dihydroxy-alpha-[(o-fluorophenylamino)methyl]-benzyl alcohol
3,4-dihydroxy-alpha-[(p-fluorophenylamino)methyl]-benzyl alcohol
3,4-dihydroxy-alpha-[(o-chlorophenylamino)methyl]-benzyl alcohol
3,4-dihydroxy-alpha-[(p-bromophenylamino)methyl]-benzyl alcohol
3,4-dihydroxy-alpha-[(2'-chloro-4'-methylphenylamino)methyl]-benzyl alcohol
3,4-dihydroxy-alpha-[(p-trifluoromethylphenylamino)methyl]-benzyl alcohol
3,4-dihydroxy-alpha-[(2',6'-dichlorophenylamino)methyl]-benzyl alcohol
3,4-dihydroxy-alpha-[(2',4',5'-trichlorophenylamino)methyl]-benzyl alcohol 3,4-dihydroxy-alpha-[(pentafluorophenylamino)methyl]-benzyl alcohol
3,4-dihydroxy-alpha-[(o-methoxyphenylamino)methyl]-benzyl alcohol
3,4-dihydroxy-alpha-[(p-methoxyphenylamino)methyl]-benzyl alcohol
3,4-dihydroxy-alpha-[(o-phenoxyphenylamino)methyl]-benzyl alcohol
3,4-dihydroxy-alpha-[(p-phenoxyphenylamino)methyl]-benzyl alcohol
3,4-dihydroxy-alpha-[(cycloheptylamino)methyl]-benzyl alcohol
3,4-dihydroxy-alpha-[(cyclohexenylamino)methyl]-benzyl alcohol
3,4-dihydroxy-alpha-[(phenethylamino)methyl]-benzyl alcohol
3,4-dihydroxy-alpha-[(cyclopropylcarbinylamino)methyl]-benzyl alcohol
3,4-dihydroxy-alpha-[(1-naphthylamino)methyl]-benzyl alcohol
3,4-dihydroxy-alpha-[(2-naphthylamino)methyl]-benzyl alcohol
3,4-dihydroxy-alpha-[(biphenylylamino)methyl]-benzyl alcohol
3,4-dihydroxy-2-methyl-alpha-[(methylamino)methyl]-benzyl alcohol
3,4-dihydroxy-2,5-dimethyl-alpha-[(ethylamino)methyl]-benzyl alcohol
3,4-dihydroxy-2-phenyl-alpha-[(methylamino)methyl]-benzyl alcohol
3,4-dihydroxy-2-phenoxy-alpha-[(butylamino)methyl]-benzyl alcohol
3,4-dihydroxy-5-methyl-alpha-[(phenylamino)methyl]-benzyl alcohol
3,4-dihydroxy-5-phenyl-alpha-[(cyclohexylamino)methyl]-benzyl alcohol
3,4-dihydroxy-2-methoxy-alpha-[(ethylamino)methyl]-benzyl alcohol
3,4-dihydroxy-2-chloro-5-ethyl-alpha-[(decylamino)methyl]-benzyl alcohol
3,4-dihydroxy-2-trifluoromethyl-alpha-[(dodecenylamino)methyl]benzyl alcohol
3,4-dihydroxy-2,5-difluoro-alpha-[(phenethylamino)methyl]-benzyl alcohol
3,4-dihydroxy-2-fluoro-alpha-[(methylamino)methyl]-benzyl alcohol In another embodiment of this invention there is provided a process for the production of compounds of Formula I above which comprises:

a) acylating a 1,2-benzenediol, such as catechol, by reaction with alpha-haloacetic acid or an alpha-haloacetic acid derivative in the presence of a Lewis acid catalyst to form a haloacetophenone compound of the formula

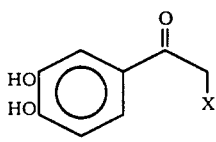

(III)

where X is a halogen atom;

b) reacting such haloacetophenone compound with ammonia or a primary monoamine, RNH$_2$, where R is as defined above, to form a compound of the formula

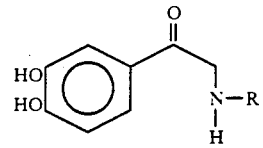

(IV)

and c) subjecting compound of Formula IV above to selective hydrogenolysis using hydrogen and a metal hydrogenolysis catalyst in the manner described hereinabove such that a compound of Formula I above is produced.

Among suitable 1,2-benzenediols which may be used in this embodiment of the invention are catechol, 3-methylcatechol, 3-ethylcatechol, 3-(2-octyl)catechol, 3-methoxycatechol, 3-ethoxycatechol, 3-phenoxycatechol, 3-(chlorophenoxy)catechol, 3-chlorocatechol, 3-fluorocatechol, 3-allylcatechol, 3,6-dimethylcatechol, 3,6-diisopropylcatechol, 3-chloro-6-methylcatechol, 3-trifluoromethylcatechol, 3-trifluoromethylcatechol, 3,6-diphenoxycatechol, and the like.

Acylation pursuant to step a) is effected by use of such acylating agents as 2-chloroacetic acid, 2-bromoacetic acid, 2-iodoacetic acid, 2-chloroacetic anhydride, 2-bromoacetic anhydride, 2-chloroacetyl chloride, 2-bromoacetyl chloride, and the like. It has been found that higher yields can be achieved using the anhydrides. The reaction conditions used in such acylation reactions are conventional. See for example Buu-Hoi et al, *J. Org. Chem.* 1950, 20, 606, all disclosure of which is incorporated herein by reference.

Lewis acid catalysts which may be employed in step a) are typified by boron trifluoride, aluminum chloride, zinc chloride, ferric chloride, titanium tetrachloride, stannic chloride, and the like.

Ammonia or any of a wide variety of primary monoamines may be used in step b) above. These amines include methylamine, ethylamine, butylamine, octylamine, isopropylamine, cyclohexylamine, 3,4-dimethylcyclohexylamine, fluorocyclohexylamine, aniline, 4-trifluoromethylaniline, 4-methoxyaniline, ethoxyethylamine, 2,2-(diethoxy)ethylamine, laurylamine, allylamine, 4-aminobiphenyl, and the like.

The reaction conditions used in substitution reaction b) are conventional. For example recourse made be had to procedures such as described by Stolz, *Chem. Ber.*, 1904, 37, 4149, all disclosure of which is incorporated herein by reference.

The practice and advantages of this invention will become still further apparent from the following illustrative examples. This invention is not limited to, and is not to be limited by, the particulars described therein. Examples 1 and 2 illustrate the process of this invention wherein compounds of Formula II above are readily and smoothly converted into compounds of Formula I above by the hydrogenolysis process of this invention.

EXAMPLE 1

Epinine Hydrochloride by Hydrogenolysis of Adrenalone

To 110 mg (0.49 mmol) adrenalone hydrochloride dissolved in 5.0 g 5% aq HCl was added 27 mg 10% Pd/C catalyst. This was shaken for 20 hr at 50 psig hydrogen in a Parr Hydrogenation Apparatus heated at 67° C. After cooling, the mixture was vacuum filtered and then evaporated. A 91% yield was measured by proton NMR spectroscopy using the internal standard N,N-dimethylbenzylamine. $^{13}$C NMR (75 MHz, D$_2$O, TSP): 145.0, 143.8, 129.8, 122.0, 117.3, 51.0, 33.6, 31.7; $^1$H NMR (300 MHz, D$_2$O, TSP): 6.90 (d, J=8 Hz, 1 H), 6.84 (d, J=3 Hz, 1 H), 6.74 (dd, J=8, 3 Hz, 1 H), 3.24 (t, J=8 Hz, 2 H), 2.88 (t, J=8 Hz, 2 H), 2.72 (s, 3 H), 1.71 (bs, 2 H).

EXAMPLE 2

Epinine Hydrochloride by Hydrogenolysis of Epinephrine

To 2.0 g (11 mmol) epinephrine was added 20 g 5% aq HCL and 0.40 g 10% palladium on carbon. This was heated at 60° C. under 50 psi H$_2$ in Parr hydrogenator for 24 hr. The reaction mixture was vacuum filtered then evaporated to afford a yellow oil which crystallized upon standing over a several day period. By proton NMR spectroscopy, this was determined to be a hydrate of the hydrochloride salt of epinine, with no traces of the starting material, epinephrine.

Examples 3 and 4 illustrate, respectively, typical procedures for performing steps a) and b) hereinabove.

EXAMPLE 3

Acylation of Catechol with alpha-Chloroacetic Acid Anhydride

To 10 g (91 mmol) catechol was added 17 g (96 mmol) chloroacetic acid anhydride and 16 mL diethyl ether. A stream of boron trifluoride was passed over this for 45 min while the reaction mixture was rapidly stirred, chilled in an ice bath. This was allowed to warm to room temperature, then after 16 hr the boron complex was decomposed with 36 mL of water. Heat was evolved. This was allowed to stand for 1 hr, vacuum filtered, then rinsed with water and methylene chloride. A dark purple powder (3,4-dihydroxy-alpha-chloroacetophenone) weighing 11 g (66% yield) was obtained, which was used without further purification in the subsequent methamination step of Example 4. $^{13}$C NMR (75 MHz, D-DMSO, TSP): 190.9, 152.6, 146.6, 127.2, 123.1, 116.3, 48.2; $^1$H NMR (300 MHz, D-DMSO, TSP): 7.42 (dd, J=8, 2 Hz, 1 H), 7.39 (d, J=2 Hz, 1 H), 6.87 (d, J=8 Hz, 1 H), 5.02 (s, 2 H), 3.57 (bs, 2 H).

EXAMPLE 4

3,4-Dihydroxy-alpha-Methylaminoacetophenone from 3,4-Dihydroxy-alpha-chloroacetophenone and Methylamine To 1.4 g (7.6 mmol) 3,4-dihydroxy-alpha-chloroacetophenone was added 0.70 mL ethanol then dropwise 4.2 mL 40% aq methylamine (48 mmol). This reaction mixture became a yellowish-brown immediately. It was heated at 50° C. for 2.5 hr then allowed to stand at room temperature for 20 hr more. The precipitate was vacuum filtered, rinsing with ethanol (chilled at 0° C.). A tan powder weighing 0.96 g was collected, which corresponded to a 70% yield of the hydrochloride salt of adrenalone. $^{13}$C NMR (75 MHz, D-DMSO, TSP): 191.6, 153.6, 147.1, 127.1, 123.5, 116.4, 54.6, 34.1; $^1$H NMR (300 MHz, D-DMSO, TSP): 7.50 (d, J=2 Hz, 1 H), 7.45 (dd, J=9, 2 Hz, 1 H), 6.98 (d, J=9 Hz, 1 H), 5.44 (s, 3 H), 4.67 (s, 2 H), 2.70 (s, 3 H).

Procedures that may be used for converting compounds of Formula I above into other useful products are illustrated in ensuing Examples 5-9. The procedures of Examples 6-9 typify processes described more fully in the co-pending applications referred to hereinabove.

EXAMPLE 5

5,6-Diacetoxy-N-methylindole by Oxidatively Cyclizing Epinine with Potassium Ferric Cyanide To 50 mg (0.24 mmol) 96% epinine hydrochloride dissolved in 3.9 g of water was dropwise added 3.5 g of a potassium ferric cyanide solution (5.2 g K$_3$Fe(CN)$_6$ plus 1.7 g NaHCO$_3$ plus 50 g water), affording immediately a deep red solution. After 5 min 1.9 g of 20% aq Zn(OAc)$_2$ and 15 mL of ethyl acetate were added with rapid stirring, to give a grey-black slush. This was Schlenk-filtered under N$_2$. The layers were partitioned and the aqueous fraction was extracted with four 15 mL portions of ether. The combined organic extracts were dried over sodium sulfate then evaporated to 1 mL. To this was added 5.0 g of acetic anhydride and 2 mg of N,N-dimethylaminopyridine (DMAP). This was heated with stirring at 60° C. for 1 hr, then allowed to cool for 20 hr more. The reaction mixture was taken up in a 50 mL portion of ethyl acetate and washed with 20 mL portions of brine, 5% aq. HCl, 3% aq NaHCO$_3$ and brine again. It was dried over sodium sulfate and then evaporated to yield 24 mg (42%) of a light yellow crystalline material, which was found by proton NMR spectroscopy to be clean 5,6-diacetoxy-N-methylindole (DAMI).

EXAMPLE 6

5,6-Diacetoxy-N-methylindole by Oxidative Cyclization Epinine with Manganese Dioxide Followed by Isomerization with Alumina To 51 mg (0.20 mmol) 79% epinine hydrochloride dissolved in 3.7 g pH 6 phosphate buffer (100 mL of 0.10 M aq KH$_2$PO$_4$ plus 11.2 mL of 0.10 N aq NaOH) was added 0.27 g (3.10 mmol) of activated manganese dioxide. After 2 min, this red mixture was Schlenk-filtered under N$_2$ into a mixture of 2.0 g of aluminum oxide (Alumina Adsorption by Fischer)—previously washed with water—plus 10 mL of ethyl acetate. After 1 hr of rapid stirring, nearly all of the pink coloring had faded. This was Schlenk-filtered again, and the bilayer was partitioned. The aqueous fraction was extracted with four 15 mL portions of ethyl acetate. The organic fractions were combined, then dried over sodium sulfate. They were evaporated to ca. 2 mL then acetylated as in Example 5 using 2.0 g acetic anhydride plus 2 mg DMAP. An identical workup was employed, yielding 30 mg (61% yield) of yellow crystals of DAMI which were nearly pure by proton NMR.

EXAMPLE 7

5,6-Diacetoxy-N-Methylindole by Oxidative Cyclization of Epinine with Manganese Dioxide Followed by Isomerization with Zinc Acetate The above-detailed manganese dioxide oxidation was effected on 51 mg (0.20 mmol) 79% epinine hydrochloride, yielding a deep red solution of epinochrome. This was isomerized over a mixture of 0.56 g (2.5 mmol) of zinc acetate and 15 mL of ethyl acetate. After 45 min of rapid stirring, this mixture was yet slightly pink. It was again Schlenk-filtered under N$_2$, then it was partitioned. Extractions and drying were performed as in Example 5. After an identical acetylation process, 31 mg (63% yield) of DAMI was collected.

EXAMPLE 8

5,6-Diacetoxy-N-Methylindole by Oxidative Cyclization of Epinine with Manganese Dioxide Followed by Isomerization with Amberlyst ®A-21

The above-detailed manganese dioxide oxidation was effected on 50 mg (0.19 mmol) of 79% epinine hydrochloride, yielding a deep red solution of epinochrome. This was isomerized over 2.0 g water-washed Amberlyst ®A-21 and 10 mL ethyl acetate. After 30 min of rapid stirring, this mixture had a slight yellowish hue. It was again Schlenk-filtered under N₂, then it was partitioned. Extractions and drying as above were performed. After an identical acetylation process, 25 mg (52% yield) of DAMI was collected.

EXAMPLE 9

5,6-Diacetoxy-N-Methylindole by Oxidative Cyclization of Epinine with Manganese Dioxide Followed by Isomerization in the Presence of Acetic Anhydride.

To 56 mg (0.22 mmol) of 79% epinine hydrochloride in 5.0 g buffer (100 mL of 0.10 M aq KH₂PO₄ plus 11.2 mL of 0.10 N aq NaOH) was added 0.26 g (3.0 mmol) of manganese dioxide. After 1.5 min, this mixture was Schlenk-filtered through Celite under N₂. The red effluent was rapidly stirred with 15 mL of ethyl acetate and 2.0 g of acetic anhydride for 60 min. Then 2.0 g of water-washed Amberlyst ® A-21 was added, and the mixture was stirred for a second hour while the red hue slowly faded. The reaction mixture was again Schlenk filtered. The phases were partitioned, and the aqueous fraction was extracted with three 30 mL portions of ethyl acetate. The organic fractions were combined, dried over sodium sulfate then evaporated. The residue was treated with 2.0 g of acetic anhydride and 2 mg of N,N-dimethylaminopyridine. This was heated at 60° C. for 90 min. The reaction mixture was taken up in a 50 mL portion of ethyl acetate and washed with 30 mL portions of brine, 5% aq HCl, 3% aq sodium bicarbonate and brine again. It was dried over sodium sulfate then evaporated to afford 43 mg of brown crystals corresponding to an 80% yield of DAMI which was clean by proton NMR spectroscopy.

This invention is susceptible to considerable variation in its practice within the spirit and scope of the ensuing claims.

What is claimed is:

1. A process which comprises subjecting one or more compounds of the formula

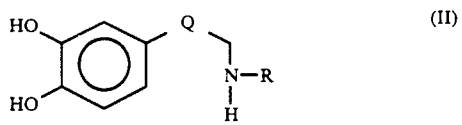

where Q is either a carbonyl group

or a hydroxymethylene group

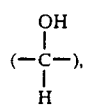

and R is a hydrogen atom or a hydrocarbyl group, to hydrogenolysis in an aqueous, acidic reaction medium at a temperature of about 20° to about 100° C. and a pressure up to about 100 psi using hydrogen and a metal hydrogenolysis catalyst such that there is produced a compound of the formula

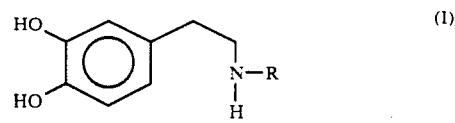

wherein R is a hydrogen atom or a hydrocarbyl group.

2. A process according to claim 1 wherein the catalyst is a palladium, platinum, rhodium or nickel catalyst.

3. A process according to claim 2 wherein the catalyst is a supported catalyst.

4. A process according to claim 1 wherein the catalyst is palladium supported on carbon.

5. A process according to claim 1 wherein the compound of Formula (II) has at least one hydrocarbon sustituent in the 3 or 6 position of the aromatic ring.

6. A process according to claim 1 wherein the compound of Formula (II) is devoid of substituents other than hydrogen atoms in the 3, 5 and 6 positions of the aromatic ring.

7. A process according to claim 1 wherein Q is a carbonyl group.

8. A process according to claim 7 wherein the compound of Formula (II) is adrenalone.

9. A process according to claim 8 wherein the catalyst is a palladium-carbon catalyst and wherein the hydrogenolysis is conducted in a non-oxidizing acidic liquid reaction medium.

10. A process according to claim 9 wherein the hydrogenolysis is conducted in an aqueous hydrochloric acid reaction medium.

11. A process according to claim 1 wherein Q is a hydroxymethylene group.

12. A process according to claim 11 wherein the compound of Formula (II) is epinephrine.

13. A process according to claim 12 wherein the catalyst is a palladium-carbon catalyst and wherein the hydrogenolysis is conducted in a non-oxidizing acidic liquid reaction medium.

14. A process according to claim 13 wherein the hydrogenolysis is conducted in an aqueous hydrochloric acid reaction medium.

* * * * *